United States Patent [19]
Cherkofsky

[11] 3,954,995
[45] May 4, 1976

[54] MONO-AND DISUBSTITUTED HYDROXYGUANIDINES IN THE TREATMENT OF DEPRESSION

[75] Inventor: Saul Carl Cherkofsky, Wilmington, Del.

[73] Assignee: E. I. Du Pont de Nemours and Company, Wilmington, Del.

[22] Filed: Apr. 16, 1974

[21] Appl. No.: 461,390

Related U.S. Application Data

[63] Continuation-in-part of Ser. No. 350,119, April 11, 1973, abandoned, which is a continuation-in-part of Ser. No. 283,775, Aug. 25, 1972, abandoned.

[52] U.S. Cl.............................. 424/326; 260/564 A

[51] Int. Cl.$^2$........................................ A61K 31/165
[58] Field of Search...................... 424/326; 260/564

[56] References Cited
OTHER PUBLICATIONS
Braun et al., Ber. *36*, pp. 3660–3663.

*Primary Examiner*—Stanley J. Friedman
*Attorney, Agent, or Firm*—Anthony P. Mentis

[57] ABSTRACT

Certain mono- and disubstituted hydroxyguanidines are useful as metal chelating agents and as antidepressants. Exemplary is 1-phenyl-1-methylhydroxyguanidine.

23 Claims, No Drawings

MONO-AND DISUBSTITUTED HYDROXYGUANIDINES IN THE TREATMENT OF DEPRESSION

RELATED APPLICATION

This application is a continuation-in-part of my commonly assigned copending application Ser. No. 350,119, filed Apr. 11, 1973, which in turn is a continuation-in-part of my commonly assigned application Ser. No. 283,775, filed Aug. 25, 1972, now abandoned.

BACKGROUND OF THE INVENTION

1. Field of the Invention

This invention relates to certain mono- and disubstituted hydroxyguanidines including selected phenyl-and benzylhydroxyguanidines, and their use as metal chelating agents and as antidepressants.

2. Prior Art

J. V. Braun and R. Schwarz, Ber., 36, 3660 (1903) describe the preparation of the hydroxyguanidines,

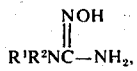

where $R^1 = C_6H_5$, $R^2 = CH_3$; $R^1 = R^2 = $ n-propyl; and $R^1 = R^2 = C_6H_5$.

In a series of papers, Belzecki and coworkers described the preparation and properties of several types of 1,1- and 1,3-disubstituted hydroxyguanidines but no examples of benzyl-substituted compounds were mentioned (C. Belzecki et al., Bull. Acad. Pol. Sci., Ser. Sci. Chim., 19 (6–7), 367 (1971); ibid, 18 (8), 431 (1970); ibid, 18 (7), 375, 379 (1970); J. Chem. Soc. D, 806 (1970) ). U.S. Pat. No. 3,505,336 discloses hydroxyguanidines of the type

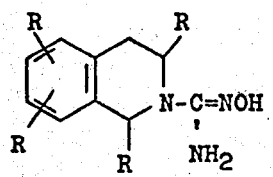

and their diacetyl derivatives as antihypertensive agents.

Certain monoalkyl-substituted hydroxyguanidine-O-sulfonic acid salts have been described (Hessing and Peppmoller, Z. Naturforsch., 22, 820 (1967) ), and 1,3-dialkylhydroxyguanidines have been prepared from 1,3-dialkylsubstituted carbodiimides (Zinner and Gross, Chem. Ber., 105, 1709 (1972) ).

Certain 1-hydroxy-2-phenylguanidines,

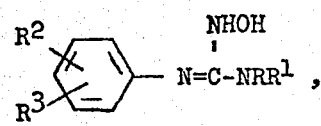

and their use as herbicides have been described (Ger. Offen. 2,040,628, Feb. 24, 1972).

SUMMARY OF THE INVENTION

It has now been found that compounds of the general formula I below are useful as metal chelating agents. The general formula is

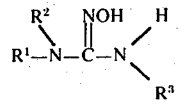

wherein
R¹ is

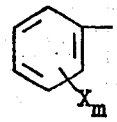

containing a total of 6–12 carbon atoms or

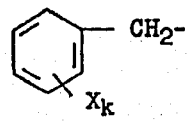

containing a total of 7–13 carbon atoms, in which

X is F, Cl, Br, $CF_3$, $NO_2$, $C_1$–$C_6$ alkyl, $C_1$–$C_6$ alkoxy, $C_1$–$C_6$ alkylthio or $C_1$–$C_6$ dialkylamino;

m = 1 to 3; and k = 0 to 3; with the proviso that no more than one $NO_2$ is present;

$R^2$ and $R^3$ individually are H, $C_1$–$C_6$ alkyl, $C_3$–$C_6$ alkenyl, an such groups containing up to two F, Cl, Br, $C_1$–$C_6$ alkoxy or $C_1$–$C_6$ dialkylamino substituents with the proviso that the unsaturated carbon atom of the alkenyl group is not directly attached to a nitrogen atom; and with the further provisos that at least one of $R^2$ and $R^3$ is hydrogen and that when $R^3$ is not hydrogen, $R^1$ is

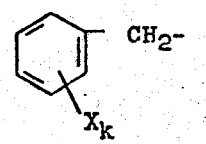

The term alkyl is intended to include cyclic alkyl groups as well as straight chain alkyl groups.

It has been found further that compounds of the general formula II below are useful as metal chelating agents and as antidepressants in the central nervous system of warm blooded animals. Their formula is

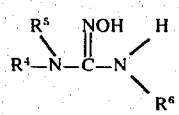

wherein
R⁴ is

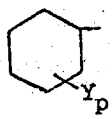

containing a total of 6–12 carbon atoms,

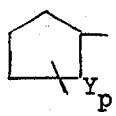

containing a total of 5–11 carbon atoms,

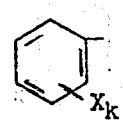

containing a total of 6–12 carbon atoms, or

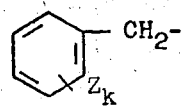

containing a total of 7–13 carbon atoms,
in which
  X is F, Cl, Br, CF$_3$, NO$_2$, C$_1$–C$_6$ alkyl, C$_1$–C$_6$ alkoxy, C$_1$–C$_6$ alkylthio or C$_1$–C$_6$ dialkylamino;
  Z is F, Cl, Br, NO$_2$, C$_1$–C$_6$ alkyl, C$_1$–C$_6$ alkoxy, C$_1$–C$_6$ alkylthio or C$_1$–C$_6$ dialkylamino;
  $k$ is 0 to 3 with the proviso that no more than one NO$_2$ is present;
  Y is F, Cl, Br, or C$_1$–C$_6$ alkyl;
  $p$ is 0 to 3;
  R$^5$ is H, methyl or ethyl with the proviso that when R$^5$ is ethyl and R$^4$ is

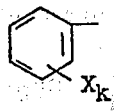

X is restricted to F, Cl, Br, CF$_3$, NO$_2$, C$_1$–C$_6$ alkoxy, C$_1$–C$_6$ alkylthio or C$_1$–C$_6$ dialkylamino; and
  R$^6$ is H, C$_1$–C$_6$ alkyl, C$_3$–C$_6$ alkenyl, and such groups containing up to two F, Cl, Br, C$_1$–C$_6$ alkoxy or C$_1$–C$_6$ dialkylamino with the proviso that the unsaturated carbon atom of the alkenyl group is not directly attached to a nitrogen atom; and with the further provisos that at least one of R$^5$ and R$^6$ is hydrogen and that when R$^6$ is not hydrogen, R$^4$ is

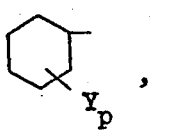 , 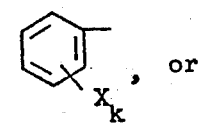 , or 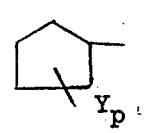

The invention also includes pharmaceutically acceptable acid addition salts of the compounds. Such salts include the hydrochloride, sulfate, nitrate, phosphate, acetate, tartrate and citrate, for example.

DETAILS OF THE INVENTION

The hydroxyguanidines of this invention are made in one of two general ways:

1. From the corresponding substituted cyanamides, R$^1$R$^2$NCN, by reaction with hydroxylamine using modifications of the procedure of von Braun and Schwarz, Ber., 36, 3660 (1903), as described below. The reaction may be considered broadly as:

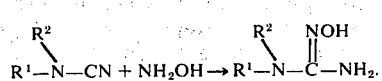

This reaction gives compounds which correspond to formula I where R$^3$ is H. When

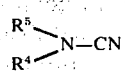

is used as the starting material, it is obvious that compounds corresponding to formula II are obtained.

2. From the corresponding carbodiimides, R$^1$N=C=NR$^3$, by reaction with hydroxylamine according to the procedure of C. Belzecki, K. Piotrowska an B. Hintze, Bull. Acad. Pol. Sci., Ser. Sci. Chim., 19 (6–7), 367 (1971). This procedure is useful when R$^3$ has a value other than hydrogen. The reaction may be depicted as:

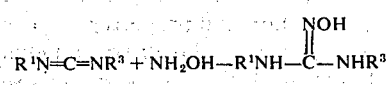

This reaction produces compounds where R$^2$ is H in formula I. It is obvious that when R$^4$—N=C=N—R$^6$ is used as the starting material compounds of formula II are produced where R$^5$ is H.

Substituted carbodiimides suitable for use in this reaction include those with the following designated groups:

TABLE I

| R$^1$ | R$^3$ |
|---|---|
| Benzyl | t-Butyl |
| Benzyl | 2,3-Dimethoxypropyl |
| p-Bromobenzyl | Isopropyl |
| Benzyl | Cyclohexyl |
| p-Chlorobenzyl | Isopropyl |
| p-Methoxybenzyl | Cyclohexyl |
| Benzyl | 2-Bromoallyl |
| p-Chlorobenzyl | Isopropyl |
| Benzyl | 2-Dimethylaminoethyl |
| Benzyl | Allyl |
| Benzyl | Crotyl |
| Benzyl | Isopropyl |
| o-Fluorobenzyl | Cyclopentyl |
| p-Nitrobenzyl | Hexyl |
| Benzyl | 2-Fluoroallyl |
| Benzyl | Methoxycyclohexyl |
| Benzyl | Cyclobutyl |
| Benzyl | 3-Butoxypropyl |
| Benzyl | 2,3-Dichloropropyl |
| Benzyl | 2-Di-n-butylaminoethyl |

TABLE 1-a

| R$^4$ | R$^6$ |
|---|---|
| Phenyl | 3-Bromopropyl |
| p-Tolyl | Ethyl |
| Cyclohexyl | Hexyl |
| p-Chlorophenyl | 3-Chloropropyl |
| m-Trifluoromethylphenyl | 3-Chloropropyl |

TABLE 1-a-continued

| R⁴ | R⁶ |
|---|---|
| Phenyl | 3-Chloropropyl |
| m-Nitrophenyl | 3-Chloropropyl |
| Cyclohexyl | Methyl |
| Phenyl | Ethyl |
| p-Methoxyphenyl | Hexyl |
| Phenyl | 2-Methoxyethyl |
| p-Dimethylaminophenyl | Ethyl |
| Cyclohexyl | Ethoxymethyl |
| p-Bromophenyl | Ethyl |
| p-Ethoxyphenyl | Ethyl |
| o-Tolyl | Methyl |

SPECIFIC EMBODIMENTS OF THE INVENTION

The following illustrative examples illustrate ways of carrying out the invention. All parts and percentages are by weight and all degrees are Centigrade unless otherwise stated.

Reaction of the substituted cyanamides of Table II with hydroxylamine using one of the procedures A, B or C, described below gives the hydroxyguanidines of Table III.

A. To a stirred mixture of 0.05 mole of substituted cyanamide and 0.05–0.1 mole (or more, if desired) of hydroxylamine hydrochloride in about 100 ml of methanol is added either all at one as a solid or over 15 minutes as a solution in methanol, 0.05–0.1 mole of potassium hydroxide. The mixture is heated under reflux for at least 2 hours. The mixture is cooled and the potassium chloride is removed by filtration. The filtrate is evaporated under reduced pressure and the residue is dissolved in about 50 ml of water containing enough concentrated hydrochloric acid to make the water layer acid ($\approx$pH 2–3). The aqueous acid layer is extracted with methylene chloride to remove any neutral impurities such as starting cyanamide and by-product urea. The aqueous acid layer is then made basic with sodium hydroxide (pH$\approx$10). If the product crystallizes, it is collected, washed with water, dried and recrystallized. If the product does not crystallize, it is removed from the aqueous layer by extraction with methylene chloride. The methylene chloride extracts are dried and the solvent evaporated. The residue is recrystallized if solid. Additionally, the hydroxyguanidine product (oil or solid) may be converted to solid HCl salt by treating a solution of the substituted hydroxyguanidine with dry HCl gas. These HCl salts can be recrystallized from methanol/ether mixtures.

B. In a variation of the above procedure, to a stirred mixture of 0.05 mole of the substituted cyanamide and 0.05 mole (or slight excess, if desired) of hydroxylamine hydrochloride in about 100 ml of methanol is added all at once a catalytic amount (about 0.1–0.5 g) of solid potassium hydroxide. The mixture is heated under reflux overnight. The cooled mixture is poured into a large volume of ether (1–2 liters) and the oily precipitate is crystallized. The white HCl salt of the product hydroxyguanidine is collected. It can be purified by recrystallization from methanol/ether, or separated and purified as the free hydroxyguanidine by addition of sodium hydroxide as described in procedure A.

C. For some hydroxyguanidines, the use of the methanol procedures, especially A, results in the formation of the isomeric aminooxyformamidine products. The use of dioxane (at reflux) in place of the methanol solvent in A sometimes avoids the formation of the isomeric by-products. Otherwise, the separation and product isolation steps are identical to those described above.

Several of the cyanamides of Table II are known and the synthesis of the others will be obvious to those skilled in the art, especially in view of the references set out in Table II.

TABLE II

Cyanamides R⁴R⁵NCN

| Used in Preparing the Compound of Example | R⁴ | R⁵ | bp (°C)(mm) | Reference |
|---|---|---|---|---|
| 1 | C₆H₅ | CH₃ | 78 (0.35) | Beilstein 12, 419 |
| 2 | C₆H₅CH₂ | CH₃ | 95 (0.2) | Beilstein 12, II 565 |
| 3 | C₆H₅CH₂ | CH₃CH₂ | 100- (0.2) .102 | W. L. Garbrecht & R. M. Herbst, J. Org. Chem. 18, 1003 (1953) |
| 4 | p-CH₃OC₆H₄CH₂ | CH₃ | 135 (0.4) | — |
| 5 | p-FC₆H₄CH₂ | CH₃ | 95 (0.2) | v. Braun et al., Ber., 63B, 2407 (1930) |
| 6 | p-BrC₆H₄CH₂ | CH₃ | 140 (0.3) | — |
| 7 | p-CH₃C₆H₄CH₂ | CH₃ | 100 (0.3) | — |
| 8 | p-NO₂C₆H₄CH₂ | CH₃ | 180 (0.15) | v. Braun et al., Ber., 70B, 1241 (1937) |
| 9 | 3,4-diClC₆H₃CH₂ | CH₃ | 133 (0.3) | — |
| 10 | p-ClC₆H₄CH₂ | CH₃ | 115 (0.3) | v. Braun et al., Ber., 63B, 2407 (1930) |
| 11 | p-ClC₆H₄ | CH₃ | mp 79 | |
| 12 | C₆H₅ | CH₃CH₂ | 82-84 (0.3) | |
| 13 | p-tolyl | CH₃ | 89-90 (0.2) | |
| 14 | p-CH₃OC₆H₄ | CH₃ | mp 58-59 | |
| 15 | m-CH₃C₆H₄ | CH₃CH₂ | 90 (0.3) | |
| 16 | p-CH₃C₆H₄ | CH₃CH₂ | 93 (0.25) | |
| 17 | C₆H₅ | n-propyl | 92-3 (0.3) | |
| 18 | cyclohexyl | CH₃ | 65 (0.1) | |
| 19 | C₆H₅CH₂ | H | mp 44-46 | Beilstein 12, 1051 |
| 20 | m-ClC₆H₄CH₂ | CH₃ | 109 (0.2) | |
| 21 | m-NO₂C₆H₄CH₂ | CH₃ | 175 (0.2) | |
| 22 | m-ClC₆H₄ | CH₃ | mp 79-81 | |
| 23 | 3,4-diCH₃C₆H₃ | CH₃ | mp 55-56 | |
| 24 | m-CH₃C₆H₄ | CH₃ | 87 (0.08) | |
| 25 | Cyclopentyl | CH₃ | 63 (0.6) | |

TABLE III

| Example | Compound |
|---|---|
| 1 | 1-phenyl-1-methylhydroxyguanidine |
| 2 | 1-benzyl-1-methylhydroxyguanidine |
| 3 | 1-benzyl-1-ethylhydroxyguanidine |
| 4 | 1-p-methoxybenzyl-1-methylhydroxyguanidine |
| 5 | 1-p-fluorobenzyl-1-methylhydroxyguanidine |
| 6 | 1-p-bromobenzyl-1-methylhydroxyguanidine |
| 7 | 1-p-methylbenzyl-1-methylhydroxyguanidine |
| 8 | 1-p-nitrobenzyl-1-methylhydroxyguanidine |

TABLE III-continued

| Example | Compound |
|---|---|
| 9 | 1-(3,4-dichlorobenzyl)-1-methylhydroxyguanidine |
| 10 | 1-p-chlorobenzyl-1-methylhydroxyguanidine |
| 11 | 1-p-chlorophenyl-1-methylhydroxyguanidine |
| 12 | 1-phenyl-1-ethylhydroxyguanidine |
| 13 | 1-p-tolyl-1-methylhydroxyguanidine |
| 14 | 1-p-methoxyphenyl-1-methylhydroxyguanidine |
| 15 | 1-m-tolyl-1-ethylhydroxyguanidine |
| 16 | 1-p-tolyl-1-ethylhydroxyguanidine |
| 17 | 1-phenyl-1-n-propylhydroxyguanidine |
| 18 | 1-cyclohexyl-1-methylhydroxyguanidine |
| 19 | 1-benzylhydroxyguanidine |
| 20 | 1-m-chlorobenzyl-1-methylhydroxyguanidine |
| 21 | 1-m-nitrobenzyl-1-methylhydroxyguanidine |
| 22 | 1-m-chlorophenyl-1-methylhydroxyguanidine |
| 23 | 1-(3,4-xylyl)-1-methylhydroxyguanidine |
| 24 | 1-m-tolyl-1-methylhydroxyguanidine |
| 25 | 1-cyclopentyl-1-methylhydroxyguanidine |

TABLE IV

Substituted Hydroxyguanidines, $R^1R^2N\overset{\overset{NOH}{\|}}{C}-NHR^3$

| $R^1$ | $R^2$ | $R^3$ |
|---|---|---|
| p-Tolyl | H | H |
| p-Chlorobenzyl | H | H |
| Benzyl | H | t-Butyl |
| Benzyl | H | 2,3-Dimethoxypropyl |
| p-Bromobenzyl | H | Isopropyl |
| Benzyl | H | Cyclohexyl |
| p-Chlorobenzyl | H | Isopropyl |
| p-Methoxybenzyl | H | Cyclohexyl |
| Benzyl | H | 2-Bromoallyl |
| p-Chlorobenzyl | H | Isobutyl |
| Benzyl | H | 2-Dimethylaminoethyl |
| Benzyl | H | Allyl |
| Benzyl | H | Crotyl |
| Benzyl | H | Isopropyl |
| o-Fluorobenzyl | H | Cyclopentyl |
| p-Nitrobenzyl | H | Hexyl |
| Benzyl | H | 2-Fluoroallyl |
| Benzyl | H | Methoxycyclohexyl |
| Benzyl | H | Cyclobutyl |
| Benzyl | H | 3-Butoxypropyl |
| Benzyl | H | 2,3-Dichloropropyl |
| Benzyl | H | 2-Di-n-butylaminoethyl |
| 3,5-Dimethylbenzyl | Ethyl | H |
| 2,4,6-Trimethoxybenzyl | Methyl | H |
| o-Fluorobenzyl | Cyclohexyl | H |
| m-Bromobenzyl | Allyl | H |
| p-Ethoxybenzyl | Hexyl | H |
| m-Ethylbenzyl | $BrCH_2CH_2CH_2$ | H |
| 2-Chloro-4-methoxyphenyl | $FCH_2CH_2CH_2$ | H |
| Benzyl | Cyclopentyl | H |
| Benzyl | Cyclopropyl | H |
| p-Dimethylaminobenzyl | $CH_3OCH_2CH_2CH_2CH_2$ | H |
| p-n-Hexylthiobenzyl | $C_2H_5OCH_2CH_2$ | H |
| p-n-Butylthiobenzyl | $ClCH_2CH_2CH_2CH_2$ | H |

TABLE IVa

Substituted Hydroxyguanidines, $R^4R^5N\overset{\overset{NOH}{\|}}{C}-NHR^6$

| $R^4$ | $R^5$ | $R^6$ |
|---|---|---|
| Phenyl | H | H |
| Phenyl | H | 3-Bromopropyl |
| p-Tolyl | H | Ethyl |
| p-Methylcyclohexyl | H | Hexyl |
| p-Chlorophenyl | H | 3-Chloropropyl |
| m-Trifluoromethylphenyl | H | 4-Chlorobutyl |
| Phenyl | H | 3-Chloropropyl |
| m-Nitrophenyl | H | 3-Chloropropyl |
| m-Chlorocyclohexyl | H | Methyl |
| Phenyl | H | Ethyl |
| p-Methoxyphenyl | H | Hexyl |
| Phenyl | H | 2-Methoxyethyl |
| p-Dimethylaminophenyl | H | Ethyl |
| 2,4-Dimethyl-6-chlorocyclohexyl | H | Ethoxymethyl |

TABLE IVa-continued

Substituted Hydroxyguanidines, $R^4R^5N\overset{\overset{NOH}{\|}}{C}-NHR^6$

| $R^4$ | $R^5$ | $R^6$ |
|---|---|---|
| p-Bromophenyl | H | $CH_2=CHCH_2CH_2CH_2$ |
| p-Ethoxyphenyl | H | Ethyl |
| o-Tolyl | H | Methyl |
| p-n-Butylcyclohexyl | H | i-Propyl |
| 2,4,6-Trichlorobenzyl | Methyl | H |
| p-Isopropylphenyl | Methyl | H |
| p-Trifluoromethylphenyl | Methyl | H |
| 2-Methyl-4-methoxybenzyl | Ethyl | H |
| 2,4-Dichlorophenyl | Ethyl | H |
| p-Trifluoromethylphenyl | Ethyl | H |

EXAMPLE 26

1-Phenyl-3-methyl-2-hydroxyguanidine

A mixture of 6.6 g (0.04 mole) of 1-phenyl-3-methyl-thiourea and 17.3 g (0.08 mole) of yellow mercuric oxide in 50 ml of ether was stirred vigorously at room temperature for 0.5 hour. The thick slurry was diluted with additional ether and filtered. To the filtrate was added all at once a solution of hydroxylamine prepared by treating 3.5 g (0.05 mole) of hydroxylamine hydrochloride in 50 ml of methanol at 0° with 2.8 g (0.05 mole) of potassium hydroxide (filtered after 0.5 hour to remove potassium chloride). The ether-methanol solution of the carbodiimide and hydroxylamine was stirred for 0.5 hour, then the solvent was removed at reduced pressure. The residue was dissolved in dilute hydrochloric acid and extracted with methylene chloride to remove neutral impurities. The aqueous layer was then made basic with sodium hydroxide. Extraction with methylene chloride and removal of the solvent gave the crude product. It was recrystallized from methylene chloride/hexane to give 1.3 g of white 1-phenyl-3-methyl-2-hydroxyguanidine, mp 95°–6°; nmr (CDCl$_3$): δ 2.7 (s, 3); 6.9–7.4 (m, 5); 4–7 (very broad, 3). IR (chloroform solution): both OH and NH present. In the antitetrabenazine test, this compound gave a ptosis ED$_{50}$ of 12.2 mg/kg and exploratory ED$_{50}$ of > 81 mg/kg.

EXAMPLE 27

1-Benzyl-3-methyl-2-hydroxyguanidine

Using the procedure of Example 26, from 7.2 g (0.04 mole) of 1-benzyl-3-methylthiourea, there was prepared 0.8 g of 1-benzyl-3-methyl-2-hydroxyguanidine, obtained as a white crystalline solid, mp 97°–9°; nmr (CDCl$_3$): δ 2.65 (s, 3); 4.2 (s, 2); 7.3 (s, 5); 4–6 (very broad, 3). IR(chloroform solution): both OH and NH present. This compound was inactive in the antitetrabenazine screen at up to 81 mg/kg.

All the aromatic hyroxyguanidines of this invention are useful as metal complexing agents. The hydroxyguanidines in solution will extract metal cations from solution and thus can be used to separate and recover valuable metals from their salts. The following examples illustrate this utility.

EXMPLE A

Aqueous solutions of cobaltous nitrate and cupric acetate were prepared by dissolving 1 g of the compound in 10 ml of water. To 1 ml of each solution was added a few drops of an aqueous solution of 1-phenyl-1-methylhydroxyguanidine, prepared by dissolving 0.2 g of the hydroxyguanidine in 10 ml of water. Immediate color changes were noted with formation of precipitates; the cobalt precipitate was dark green-brown and the copper precipitate dark green. The aqueous mixtures were extracted with 2-butanol and highly colored organic layers were separated illustrating the extraction of the metal ions from aqueous solution.

When the experiment was repeated in methanol solution with tetraisopropyl titanate a bright yellow complex of titanium with the hydroxyguanidine was formed.

EXAMPLE B

The experiment of Example A was repeated with 1-benzyl-1-methylhydroxyguanidine and similar cobalt, copper and titanium complexes were obtained.

EXAMPLE C

The experiment of Example A was repeated with 1-benzyl-1-propylhydroxyguanidine and similar extractable complexes of cobalt, copper and titanium were obtained.

The compounds of this invention are also useful as antidepressant agents. They can be employed in pharmaceutical compositions composed of the active ingredient, i.e., the compound(s) of the invention, in combination with non-toxic pharmaceutical carriers and additives. In any formulation of the antidepressant agent, the active ingredient will ordinarily be present in an amount from about 0.5% to 95% based on total weight of the composition.

Formulations include injectables and oral dosage forms such as tablets, hard and soft gelatin capsules, suspensions, syrups, elixirs and the like. Additives that can be employed in such formulations include solvents and diluents, lubricants, binding agents, disintegrants, preservatives, colorants, flavors and other additives which are common and well known to the art and which form no part of this invention.

The compounds of this invention can be administered as treatment for psychiatric depressions of the reactive and endogenous types by any means that effects contact of the active ingredient compound with the site of action in the body of a warm-blooded animal. For example, administration can be parenterally, i.e., subcutaneously, intravenously, intramuscularly or intraperitoneally. Alternatively or concurrently, administration can be by the oral route.

The dosage administered will be dependent upon the age, health and weight of the recipient, the type and severity of depression, kind of concurrent treatment, if any, frequency of treatment and the nature of the effect desired. Generally a daily dosage of active ingredient compound will be from about 0.01 to 50 mg/kg or body weight. Ordinarily, from 0.05 to 40 and preferably 0.1 to 20mg/kg per day in one or more applications per day is effective to obtain desired results. For the more potent compounds of the invention, e.g., the compound of Example 2, the daily dosage ranges from about 0.01 to 20 mg/kg, preferably 0.05 to 10 mg/kg, and more preferably 0.1 to 5 mg/kg.

The pharmaceutical carrier can be a sterile liquid such as water, or an oil, e.g., petroleum oil, animal oil, or vegetable oils such as peanut oil, soybean oil, mineral oil, sesame oil, and the like. In general, water, saline, aqueous dextrose (glucose) and related sugar solutions and glycols such as propylene glycol or polyethylene glycols are preferred liquid carriers, particularly for injectable solutions. Sterile injectable solutions such as saline will ordinarily contain from about 0.05 to 25% and preferably about 1 to 10% by weight of the active ingredient.

Liquid oral administration can be in a suspension, syrup or elixir, in which the active ingredient ordinarily will constitute from about 0.5 to 10% and preferably about 1 to 5% by weight. The pharmaceutical carrier in such composition can be an aqueous vehicle such as an aromatic water, a syrup, a pharmaceutical mucilage, or a hydroalcoholic elixir. Additional information concerning pharmaceutical carriers, diluents and additives can be found in the wellknown reference text: Martin, "Remington's Pharmaceutical Sciences."

The following illustrate the preparation of pharmaceutical compositions of the invention.

EXAMPLE D

A large number of unit capsules are prepared by filling standard two-piece hard gelatin capsules each with 50 mg of powdered active ingredient, 300 mg of lactose, 32 mg of talc and 8 mg of magnesium stearate.

EXAMPLE E

A mixture of the active ingredient in soybean oil is prepared and injected by means of a positive displacement pump into gelatin to form soft gelatin capsules containing 35 mg of the active ingredient. The capsules are washed in petroleum ether and dried.

EXAMPLE F

A large number of tablets are prepared by conventional procedures so that the dosage unit is 300 mg of active ingredient, 7 mg of ethyl cellulose, 0.2 mg of colloidal silicon dioxide, 7 mg of magnesium stearate, 11 mg of microcrystalline cellulose, 11 mg of cornstarch and 98.8 g of lactose. Appropriate coatings may be applied to increase palatability or delay absorption.

EXAMPLE G

A parenteral composition suitable for administration by injection is prepared by stirring 1.5% by weight of the active ingredient in 10% by volume propylene glycol and water. The solution is sterilized by filtration.

EXAMPLE H

An aqueous suspension is prepared for oral administration so that each 5 ml contains 50 mg of finely divided active ingredient, 500 mg of acacia, 5 mg of sodium benzoate, 1.0 g of sorbitol solution, U.S.P., 5 mg of sodium saccharin and 0.025 ml of vanilla tincture.

EXAMPLE I

A parenteral composition suitable for administration by injection is prepared by dissolving 1% by weight of the active ingredient as the maleate salt in sodium chloride injection U.S.P. and adjusting the pH of the solution to between 6 and 7. The solution is sterilized by filtration.

The antidepressant activity of the compounds of the invention is evidenced by tests conducted in female white mice in which prevention of tetrabenazine-induced sedation and depression was demonstrated. This mouse test is predictive of human antidepressant response (Everett, G. M., "The Dopa Response Potentiation Test and Its Use in Screening for Antidepressant Drugs", pp. 164–167 in "Antidepressant Drugs", Proceedings of the First International Symposium, S. Garattini and M. N. G. Dukes, eds., 1967).

EXAMPLE J

Groups of 10 Carworth $CF_1S$ female mice, 18–21 g each, were fasted 1.5 hours and were intubated with a hydroxyguanidine as antagonist to tetrabenazine at oral doses of 5, 25 and 125 mg/kg in 0.20 ml of 1% methyl cellulose (Methocel.) Thirty minutes later the mice were challenged with tetrabenazine, 32 mg/kg intraperitoneally (dissolved in 0.20 ml of 0.05M KCl at pH 2.0). One hour after the hydroxyguanidine compound (30 minutes after tetrabenzine) the mice were examined for signs of exploratory activity and ptosis (eye-lid closure). Normal exploratory activity (relief from sedation) was recorded when a mouse lifted by the tail from a group of 10 in a testing box and placed on a stainless steel testing box lid (12.5 inch × 8 inch × 0.33 inch mesh) either turned its head horizontally 30° or moved to the edge of the screen withi 10 seconds after being placed on the screen. Relief from ptosis was recorded when exactly 2 seconds after placing the mouse facing the observer, lid closure was less than 50% in both eyes.

With relief of ptosis as the criterion, the hydroxyguanidine of Example 2 and several related compounds are potent in preventing tetrabenazine-induced sedation in mice. The ptosis ED 50, i.e., the dose which blocked ptosis in 50% of the mice, for the compound of Example 2 was 0.18 (0.04–0.32) mg/kg.

Table V

Hydroxyguanidines and Their Physical and Antidepressant Properties, $R^4R^5N\overset{\overset{NOH}{\|}}{C}-NH_2$

| Example | Prep. Method | mp °C | H nmr (CDCl$_3$) | Analyses (Average of Determination) | Antitetrabenazine ED 50 (mg/kg) Exploratory | Ptosis |
|---|---|---|---|---|---|---|
| 1[1] | A | 98–100[1] | δ 3.1 (s,3); 5.5 (broad,3); 7.2 (m,5) | — | >81 | 1.1 |
| | A | 199–200[2] | δ 3.4 (s,3); 7.4 (m,5); very broad (3) | Calcd: C, 47.65; H, 6.00; Cl, 17.58; N, 20.84 Found: C, 46.75; H, 5.95; Cl, 17.60; N, 20.58 | 9 | 1.1 |
| 2 | A; B | 89–90 | δ 2.7 (s,3); 4.3 (s,2); 5,5 (broad, 3); 7.3 (s,5) | Calcd: C, 60.32; H, 7.31; N, 23.45 Found: C, 60.09; H, 7.25; N, 23.22 | 9 | 0.18 |
| | | 148–149[2] | | Calcd: C, 50.12; H, 6.54; Cl, 16.44; N, 19.48 Found: C, 50.28; H, 6.45; Cl, 16.31; N, 29.26 | >81 | 0.43 |
| 3 | A; C | 83.5–84.5 | δ 1.1 (t,3); 3.2 (q,2); 4.3 (s,2); ~6 (broad,3); 7.2 (s,5) | Calcd: C, 62.15; H, 7.82; N, 21.74 Found: C, 61.61; H, 7.60; N, 21.86 | 9 | 0.39 |
| 4 | B | 71–72 | δ 2.7 (s,3); 3.8 (s,3); 4.2 (s,2); 4–6 (broad,3); 7.0 ($A_2B_2$q,4) | | >81 | 59 |
| 5 | B | 101–102 | δ 2.7 (s,3); 4.25 (s,2); 4–6 (broad, 3); 6.8–7.4 (m,4) | | >81 | 8.1 |
| 6 | B | 91–92 | δ 2.7 (s,3); 4.25 (s,2); 4–6 (broad,3); 7.2 ($A_2B_2$q,4) | | >81 | 17.4 |
| 7 | B | 103–103.5 | δ 2.3 (s,3); 2.7 (s,3); 4.25 (s,2); 4–6 (broad,3); 7.1 (s,4) | | >81 | 23 |
| 8 | B | 159–160 | δ 2.7 (s,3); 4,4 (s,2); 5 (broad,3); 7.8 ($A_2B_2$q,4)[3] | | >81 | 47 |
| 9 | B | 119–120 | δ 2.7 (s,3); 4.25 (s,2) 4–6 (broad,3); 7.0–7.5 (m,3) | | >81 | 4.8 |
| 10 | B | 99–100 | δ 2.7 (s,3); 4.3 (s,2); 4–6 (broad, 3); 7.3 (~s,4) | Calcd: C, 50.59; H, 5.66; Cl, 16.59; N, 19.67 | >81 | 10.8 |

Table V-continued

Hydroxyguanidines and Their Physical and Antidepressant Properties, $R^4R^5NC(=NOH)-NH_2$

| Example | Prep. Method | mp °C | H nmr (CDCl$_3$) | Analyses (Average of Determination) | Antitetrabenazine ED 50 (mg/kg) Exploratory | Ptosis |
|---|---|---|---|---|---|---|
| 11 | A | 125–126 | δ 3.1 (s,3); 4–6 (broad,3); 7.2 (q,4) | Found: C, 50.65; H, 5.77; N, 19.93 Calcd: C, 48.13; H, 5.05; Cl, 17.76; N, 21.05 Found: C, 48.94; H, 5.03; N, 21.13 | 81 | 0.82 |
| 12 | A | 143–145 | δ 1.1 (t,3); 3.6 (q,2); 4–6 (broad, 3); 7.2 (m,5) | Calcd: C, 60.32; H, 7.31; N, 23.45 Found: C, 60.92; H, 7.21; N, 23.37 | 15.6 | 3.0 |
| 13 | A | 164–167 | δ 2.3 (s,3); 3.1 (s,3); 4–6 (broad, 3); 7.1 (s,4) | Calcd: C, 60.32; H, 7.31; N, 23.45 Found: C, 60.36; H, 7.24; N, 23.37 | 3 | 0.88 |
| 14 | A | 164–165 | δ 2.9 (s,3); 3.7 (s,3); 4.7 (broad, 2); 8.4 (broad, 1); 6.9 (A$_2$B$_2$q, 4)[3] | | >81 | 20.5 |
| 17 | A | 104–105 | δ 0.85(t,3); 1.6 (m,2); 3.5 (t,2); 4.5 (broad,3); 7.2 (m,5) | Calcd: C, 62.15; H, 7.82; N, 21.74 Found: C, 63.30; H, 7.74; N, 21.62 | >81 | 20 |
| 18 | B | 90–91 | δ 1.0–2.0 (m,10); 2.6(s,3); 3.4 (broad, 1); 5.7 (broad,3) | Calcd: C, 56.61; H, 10.01; N, 24.54 Found: C, 55.59; H, 9.27; N, 24.88 | >81 | 9 |
| 19 | B | 151–153[2] | δ 4.4(d,2); 4–8 (broad,1); 7.3(s,5); 7.8(broad,2); 8.4 (t,1); 10.7(broad,1) | Calcd: C, 47.65; H, 6.00; N, 20.84; Cl, 17.58 Found: C, 48.69; H, 6.00; N, 19.58 | >81 | 12.5 |
| 20 | B | 102–103 | δ 2.75(s,3); 4.3(s,2) 4–6 (broad,3); 7.2–7.4(m,4) | Calcd: C, 50.59; H, 5.66; N, 19.67 Found: C, 50.57; H, 5.56; N, 19.88 | >81 | 0.4 |
| 21 | B | 119–120.5 | δ 2.75(s,3); 4.5(s,2); 5.1 (broad, 3); 7.6–8.3(m,4) | Calcd: C, 48.21; H, 5.39; N, 24.99 Found: C, 47.95; H, 5.25; N, 25.11 | >81 66 | |
| 22 | A | 90–92 | δ 3.1(s,3); 6.9–7.3 (m,4); very broad[3] | Calcd: C, 48.13; H, 5.05; N, 21.05; Cl, 17.76 Found: C, 48.05; H, 5.08; N, 20.77; Cl, 17.65 | >81 | 0.7 |
| 23 | A | 152–155 | δ 2.25(s,6); 3.1(s,3); 7.1(m,3); very broad (3) | Calcd: C, 62.15; H, 7.82; N, 21.74 Found: C, 62.20; H, 7.75; N, 21.80 | >81 | 4.9 |
| 24 | A | 117–119 | δ 2.3(s,3); 3.15(s,3); 5 (broad, 3); 6.9–7.3 (m,4) | Calcd: C, 60.32; H, 7.31; N, 23.45 Found: C, 60.24; H, 7.30; N, 23.65 | >125 | 0.4 |
| 25 | A,B | 105–110[2] | δ 1.6(m,8); 2.8(s,3); 4.3 (broad, 1); 7.9 (broad, 2); 10.6 (broad, 1) | Calcd: C, 43.41; H, 8.33; N, 21.70; Cl, 18.31 Found: C, 43.59; H, 8.32; N, 21.61; Cl, 17.88 | >81 | 3 |

[1] J. von Braun and R. Schwarz, Ber., 36, 3660 (1903).
[2] Hydroxyguanidine HCl salt.
[3] nmr determined in DMSO d$_6$.

We claim:

1. A pharmaceutical composition of matter comprising an effective antidepressant amount of a compound selected from the group consisting of
   1-phenyl-1-ethylhydroxyguanidine
   1-p-chlorophenyl-1-methylhydroxyguanidine
   1-m-chlorophenyl-1-methylhydroxyguanidine
   1-p-tolyl-1-methylhydroxyguanidine
   1-m-tolyl-1-methylhydroxyguanidine and a pharmaceutically acceptable acid addition salt thereof
   in the form of an injectable, a tablet, a capsule, a syrup, an elixir or a pharmaceutical mucilage.

2. A composition of claim 1 in which the compound is 1-phenyl-1-ethylhydroxyguanidine.

3. A composition of claim 2 in which the compound is 1-benzyl-1-methylhydroxyguanidine.

4. A composition of claim 2 in which the compound is 1-benzyl-1-ethylhydroxyguanidine.

5. A composition of claim 1 in which the compound is 1-p-chlorophenyl-1-methylhydroxyguanidine.

6. A composition of claim 1 in which the compound is 1-p-tolyl-1-methylhydroxyguanidine.

7. A composition of claim 2 in which the compound is 1-cyclohexyl-1-methylhydroxyguanidine.

8. A composition of claim 2 in which the compound is 1-m-chlorobenzyl-1-methylhydroxyguanidine.

9. A composition of claim 2 in which the compound is 1-m-nitrobenzyl-1-methylhydroxyguanidine.

10. A composition of claim 1 in which the compound is 1-m-chlorophenyl-1-methylhydroxyguanidine.

11. A composition of claim 1 in which the compound is 1-m-tolyl-1-methylhydroxyguanidine.

12. A composition of claim 2 in which the compound is 1-cyclopentyl-1-methylhydroxyguanidine.

13. The method of combatting central nervous system depression in a warm blooded animal comprising the step of administering an effective antidepressant amount of a composition of claim 2 to said warm blooded animal.

14. The method of combatting central nervous system depression in a warm blooded animal comprising the step of administering an antidepressant amount of a composition of claim 3 to said warm blooded animal.

15. The method of combatting central nervous system depression in a warm blooded animal comprising the step of administering an antidepressant amount of a composition of claim 4 to said warm blooded animal.

16. The method of combatting central nervous system depression in warm blooded animal comprising the step of administering an effective antidepressant amount of a composition of claim 5 to said warm blooded animal.

17. The method of combatting central nervous system depression in a warm blooded animal comprising the step of administering an effective antidepressant amount of a composition of claim 6 to said warm blooded animal.

18. The method of combatting central nervous system depression in a warm blooded animal comprising the step of administering an antidepressant amount of a composition of claim 7 to said warm blooded animal.

19. The method of combatting central nervous system depression in a warm blooded animal comprising the step of administering an antidepressant amount of a composition of claim 8 to said warm blooded animal.

20. The method of combatting central nervous system depression in a warm blooded animal comprising the step of administering an antidepressant amount of a composition of claim 9 to said warm blooded animal.

21. The method of combatting central nervous system depression in a warm blooded animal comprising the step of administering an effective antidepressant amount of a composition of claim 10 to said warm blooded animal.

22. The method of combatting central nervous system depression in a warm blooded animal comprising the step of administering an effective antidepressant amount of a composition of claim 11 to said warm blooded animal.

23. The method of combatting central nervous system depression in a warm blooded animal comprising the step of administering an antidepressant amount of a composition of claim 12 to said warm blooded animal.

* * * * *

UNITED STATES PATENT AND TRADEMARK OFFICE
CERTIFICATE OF CORRECTION

PATENT NO. : 3,954,995
DATED : May 4, 1976
INVENTOR(S) : SAUL CARL CHERKOFSKY

It is certified that error appears in the above-identified patent and that said Letters Patent are hereby corrected as shown below:

Column 2, line 39, "an" should be --and--.

Column 4, line 26, "an" should be --and--.

Column 7, between Tables III and IV, insert:

--Examples of other hydroxyguanidines obtainable by the procedures described are shown in Table IV.--

Column 10, line 21, "or" should be --of--.

Column 13, Example 13, fourth column "4-6" should be --4.6--.

Column 13, Example 21, fourth column, delete "calcd: C, 48.21".

Column 13, Example 21, fifth column, ">81" should be --Calcd: C, 48.21--.

Column 13, Example 21, sixth column, "66" should be -->81--.

Column 13, Example 21, seventh column, insert --6--.

Columns 14, 15 and 16, delete Claims 3, 4, 7, 8, 9, 12, 14, 15, 18, 19, 20 and 23.

Signed and Sealed this

Eighth Day of February 1977

[SEAL]

Attest:

RUTH C. MASON
Attesting Officer

C. MARSHALL DANN
Commissioner of Patents and Trademarks